(12) United States Patent
Lyons (10) Patent No.: US 10,258,360 B2
(45) Date of Patent: Apr. 16, 2019

(54) SURGICAL INSTRUMENTS

(71) Applicant: COVIDIEN LP, Mansfield, MA (US)

(72) Inventor: Michael B. Lyons, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 744 days.

(21) Appl. No.: 14/806,044

(22) Filed: Jul. 22, 2015

(65) Prior Publication Data

US 2016/0089177 A1 Mar. 31, 2016

Related U.S. Application Data

(60) Provisional application No. 62/055,011, filed on Sep. 25, 2014.

(51) Int. Cl.
*A61B 17/00* (2006.01)
*A61B 17/29* (2006.01)
*A61B 18/14* (2006.01)
*A61B 17/295* (2006.01)

(52) U.S. Cl.
CPC ........ *A61B 17/295* (2013.01); *A61B 18/1445* (2013.01); *A61B 2017/00473* (2013.01); *A61B 2017/2908* (2013.01)

(58) Field of Classification Search
CPC ................................................ A61B 18/1445
See application file for complete search history.

(56) References Cited

U.S. PATENT DOCUMENTS

| D249,549 S | 9/1978 | Pike |
|---|---|---|
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |

(Continued)

FOREIGN PATENT DOCUMENTS

| CN | 201299462 | 9/2009 |
|---|---|---|
| DE | 2415263 A1 | 10/1975 |

(Continued)

OTHER PUBLICATIONS

European Search Report, dated Mar. 29, 2016, corresponding to European Application No. 15178542.5; 8 pages.

(Continued)

*Primary Examiner* — Michael F Peffley
*Assistant Examiner* — Samantha M Good (57) ABSTRACT

An electrosurgical instrument includes a housing having an elongated shaft extending therefrom and an end effector assembly coupled thereto. The housing includes a knife drive shaft and a jaw drive shaft disposed therein and movable within the elongated shaft. The end effector assembly includes a pair of opposing jaw members, a knife member, and a driven member. A proximal end of the knife member is selectively engageable to a distal end of the knife drive shaft such that movement of the knife drive shaft moves the knife member. A proximal end of the driven member is configured to operably couple to the jaw drive shaft and a distal end of the driven member is operably coupled to the jaw members to move the jaw members. A coupling member is configured to releasably secure the end effector assembly and the elongated shaft.

18 Claims, 10 Drawing Sheets

(56) References Cited

U.S. PATENT DOCUMENTS

| | | |
|---|---|---|
| D349,341 S | 8/1994 | Lichtman et al. |
| D354,564 S | 1/1995 | Medema |
| D358,887 S | 5/1995 | Feinberg |
| D384,413 S | 9/1997 | Zlock et al. |
| H1745 H | 4/1998 | Paraschac |
| D402,028 S | 12/1998 | Grimm et al. |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| 7,628,792 B2 | 12/2009 | Guerra |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| 7,837,631 B2 | 11/2010 | Diamond et al. |
| 7,842,045 B2 | 11/2010 | Vandenbroek |
| D630,324 S | 1/2011 | Reschke |
| 7,935,052 B2 | 5/2011 | Dumbauld |
| D649,249 S | 11/2011 | Guerra |
| D649,643 S | 11/2011 | Allen, IV et al. |
| 8,133,254 B2 | 3/2012 | Dumbauld et al. |
| D661,394 S | 6/2012 | Romero et al. |
| D670,808 S | 11/2012 | Moua et al. |
| D680,220 S | 4/2013 | Rachlin |
| 8,491,625 B2 | 7/2013 | Horner |
| 8,636,761 B2 | 1/2014 | Cunningham et al. |
| 2012/0101484 A1 | 4/2012 | Miersch |
| 2013/0046295 A1 | 2/2013 | Kerr et al. |
| 2013/0066230 A1 | 3/2013 | Li et al. |
| 2013/0085516 A1 | 4/2013 | Kerr et al. |
| 2013/0296848 A1 | 11/2013 | Allen, IV et al. |
| 2014/0025070 A1 | 1/2014 | Kerr et al. |
| 2014/0025071 A1 | 1/2014 | Sims et al. |
| 2014/0221999 A1 | 8/2014 | Cunningham et al. |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 3627221 A1 | 2/1988 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1281878 A1 | 2/2003 |
| EP | 1159926 A3 | 3/2003 |
| EP | 2687177 A2 | 1/2014 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 09000538 A | 1/1997 |
| JP | 9-122138 A | 5/1997 |
| JP | 0010000195 A | 1/1998 |
| JP | 10-155798 A | 6/1998 |
| JP | 11-47149 | 2/1999 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000-135222 A | 5/2000 |
| JP | 2000342599 A | 12/2000 |
| JP | 2000350732 A | 12/2000 |
| JP | 2001008944 A | 1/2001 |
| JP | 2001-29355 | 2/2001 |
| JP | 2001029356 A | 2/2001 |
| JP | 2001-03400 | 4/2001 |
| JP | 2001128990 A | 5/2001 |
| JP | 2001-190564 A | 7/2001 |
| JP | 2002-136525 A | 5/2002 |
| JP | 2002-528166 A | 9/2002 |
| JP | 2003-116871 A | 4/2003 |
| JP | 2003-175052 A | 6/2003 |
| JP | 2003245285 A | 9/2003 |
| JP | 2004-517668 A | 6/2004 |
| JP | 2004-528869 A | 9/2004 |
| JP | 2005-152663 A | 6/2005 |
| JP | 2005-253789 A | 9/2005 |
| JP | 2005312807 A | 11/2005 |
| JP | 2006-015078 A | 1/2006 |
| JP | 2006-501939 A | 1/2006 |
| JP | 2006-095316 A | 4/2006 |
| JP | 2008-054926 A | 3/2008 |
| JP | 2011125195 A | 6/2011 |
| SU | 401367 A1 | 11/1974 |

(56) References Cited

FOREIGN PATENT DOCUMENTS

| WO | 0036986 A1 | 6/2000 |
| WO | 0059392 A1 | 10/2000 |
| WO | 0115614 A1 | 3/2001 |
| WO | 0154604 A1 | 8/2001 |
| WO | 02/045589 | 6/2002 |
| WO | 06/021269 A1 | 3/2006 |
| WO | 05110264 A3 | 4/2006 |
| WO | 08/040483 A1 | 4/2008 |
| WO | 2011/018154 A1 | 2/2011 |

OTHER PUBLICATIONS

Chinese Office Action (with English translation), dated Jul. 3, 2017, corresponding to Chinese Application No. 201510589101.1; 14 total pages.

Michael Choti, "Abdominoperineal Resection with the LigaSure Vessel Sealing System and LigaSure Atlas 20 cm Open Instrument"; Innovations That Work, Jun. 2003. (4 pages).

Chung et al., "Clinical Experience of Sutureless Closed Hemorrhoidectomy with LigaSure" Diseases of the Colon & Rectum vol. 46, No. 1 Jan. 2003, pp. 87-92.

Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003. (1 page).

Peterson et al. "Comparison of Healing Process Following Ligation with Sutures and Bipolar Vessel Sealing" Surgical Technology International (2001). (8 pages).

"Electrosurgery: A Historical Overview" Innovations in Electrosurgery; Sales/Product Literature; Dec. 31, 2000. (6 pages).

Johnson et al. "Evaluation of a Bipolar Electrothermal Vessel Sealing Device in Hemorrhoidectomy" Sales/Product Literature; Jan. 2004. (1 page).

E. David Crawford "Evaluation of a New Vessel Sealing Device in Urologic Cancer Surgery" Sales/Product Literature 2000. (1 page).

Johnson et al. "Evaluation of the LigaSure Vessel Sealing System in Hemorrhoidectormy" American College of Surgeons (ACS) Clinicla Congress Poster (2000). (1 page).

Muller et al., "Extended Left Hemicolectomy Using the LigaSure Vessel Sealing System" Innovations That Work, Sep. 1999. (4 pages).

Kennedy et al. "High-burst-strength, feedback-controlled bipolar vessel sealing" Surgical Endoscopy (1998) 12:876-878.

Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.

Carus et al., "Initial Experience With the LigaSure Vessel Sealing System in Abdominal Surgery" Innovations That Work, Jun. 2002. (4 pages).

Heniford et al. "Initial Results with an Electrothermal Bipolar Vessel Sealer" Surgical Endoscopy (2000) 15:799-801. (4 pages).

Herman et al., "Laparoscopic Intestinal Resection With the LigaSure Vessel Sealing System: A Case Report"; Innovations That Work, Feb. 2002. (4 pages).

Koyle et al., "Laparoscopic Palomo Varicocele Ligation in Children and Adolescents" Pediatric Endosurgery & Innovative Techniques, vol. 6, No. 1, 2002, pp. 15-19.

W. Scott Helton, "LigaSure Vessel Sealing System: Revolutionary Hemostasis Product for General Surgery"; Sales/Product Literature 1999. (1 page).

LigaSure Vessel Sealing System, the Seal of Confidence in General, Gynecologic, Urologic, and Laparaoscopic Surgery; Sales/Product Literature; Apr. 2002. (8 pages).

Joseph Ortenberg "LigaSure System Used in Laparoscopic 1st and 2nd Stage Orchiopexy" Innovations That Work, Nov. 2002. (4 pages).

Sigel et al. "The Mechanism of Blood Vessel Closure by High Frequency Electrocoagulation" Surgery Gynecology & Obstetrics, Oct. 1965 pp. 823-831.

Sampayan et al, "Multilayer Ultra-High Gradient Insulator Technology" Discharges and Electrical Insulation in Vacuum, 1998. Netherlands Aug. 17-21, 1998; vol. 2, pp. 740-743.

Paul G. Horgan, "A Novel Technique for Parenchymal Division During Hepatectomy" The American Journal of Surgery, vol. 181, No. 3, Apr. 2001 pp. 236-237.

Benaron et al., "Optical Time-Of-Flight and Absorbance Imaging of Biologic Media", Science, American Association for the Advancement of Science, Washington, DC, vol. 259, Mar. 5, 1993, pp. 1463-1466.

Olsson et al. "Radical Cystectomy in Females" Current Surgical Techniques in Urology, vol. 14, Issue 3, 2001. (8 pages).

Palazzo et al. "Randomized clinical trial of Ligasure versus open haemorrhoidectomy" British Journal of Surgery 2002, 89, 154-157.

Levy et al. "Randomized Trial of Suture Versus Electrosurgical Bipolar Vessel Sealing in Vaginal hysterectomy" Obstetrics & Gynecology, vol. 102, No. 1, Jul. 2003, pp. 147-151.

"Reducing Needlestick Injuries in the Operating Room" Sales/Product Literature 2001. (1 page).

Bergdahl et al. "Studies on Coagulation and the Development of an Automatic Computerized Bipolar Coagulator" J. Neurosurg, vol. 75, Jul. 1991, pp. 148-151.

Strasberg et al. "A Phase I Study of the LigaSure Vessel Sealing System in Hepatic Surgery" Section of HPB Surger, Washington University School of Medicine, St. Louis MO, Presented at AHPBA, Feb. 2001. (1 page).

Sayfan et al. "Sutureless Closed Hemorrhoidectomy: A New Technique" Annals of Surgery vol. 234 No. 1 Jul. 2001; pp. 21-24.

Levy et al., "Update on Hysterectomy—New Technologies and Techniques" OBG Management, Feb. 2003. (15 pages).

Dulemba et al. "Use of a Bipolar Electrothermal Vessel Sealer in Laparoscopically Assisted Vaginal Hysterectomy" Sales/Product Literature; Jan. 2004. (1 page).

Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.

Sengupta et al., "Use of a Computer-Controlled Bipolar Diathermy System in Radical Prostatectomies and Other Open Urological Surgery" ANZ Journal of Surgery (2001) 71.9 pp. 538-540.

Rothenberg et al. "Use of the LigaSure Vessel Sealing System in Minimally Invasive Surgery in Children" Int'l Pediatric Endosurgery Group (IPEG) 2000. (1 page).

Crawford et al. "Use of the LigaSure Vessel Sealing System in Urologic Cancer Surgery" Grand Rounds in Urology 1999 vol. 1 Issue 4 pp. 10-17.

Craig Johnson, "Use of the LigaSure Vessel Sealing System in Bloodless Hemorrhoidectomy" Innovations That Work, Mar. 2000. (4 pages).

Levy et al. "Use of a New Energy-based Vessel Ligation Device During Vaginal Hysterectomy" Int'l Federation of Gynecology and Obstetrics (FIGO) World Congress 1999. (1 page).

Barbara Levy, "Use of a New Vessel Ligation Device During Vaginal Hysterectomy" FIGO 2000, Washington, D.C.. (1 page).

E. David Crawford "Use of a Novel Vessel Sealing Technology in Management of the Dorsal Veinous Complex" Sales/Product Literature 2000. (1 page).

Jarrett et al., "Use of the LigaSure Vessel Sealing System for Peri-Hilar Vessels in Laparoscopic Nephrectomy" Sales/Product Literature 2000. (1 page).

Crouch et al. "A Velocity-Dependent Model for Needle Insertion in Soft Tissue" MICCAI 2005; LNCS 3750 pp. 624-632, Dated: 2005.

McLellan et al. "Vessel Sealing for Hemostasis During Pelvic Surgery" Int'l Federation of Gynecology and Obstetrics FIGO World Congress 2000, Washington, D.C.. (1 page).

McLellan et al. "Vessel Sealing for Hemostasis During Gynecologic Surgery" Sales/Product Literature 1999. (1 page).

(56) References Cited

OTHER PUBLICATIONS

U.S. Appl. No. 08/926,869, filed Sep. 10, 1997; inventor: James G. Chandler.
U.S. Appl. No. 09/177,950, filed Oct. 23, 1998; inventor: Randel A. Frazier.
U.S. Appl. No. 09/387,883, filed Sep. 1, 1999; inventor: Dale F. Schmaltz.
U.S. Appl. No. 09/591,328, filed Jun. 9, 2000; inventor: Thomas P. Ryan.
U.S. Appl. No. 12/336,970, filed Dec. 17, 2008; inventor: Paul R. Sremcich.
U.S. Appl. No. 14/065,644, filed Oct. 29, 2013; inventor: Reschke.
U.S. Appl. No. 14/098,953, filed Dec. 6, 2013; inventor: Cunningham.
U.S. Appl. No. 14/100,237, filed Dec. 9, 2013; inventor: Reschke.
U.S. Appl. No. 14/103,971, filed Dec. 12, 2013; inventor: Roy.
U.S. Appl. No. 14/105,374, filed Dec. 13, 2013; inventor: Moua.
U.S. Appl. No. 14/152,618, filed Jan. 10, 2014; inventor: Artale.
U.S. Appl. No. 14/152,690, filed Jan. 10, 2014; inventor: Hart.
U.S. Appl. No. 14/169,358, filed Jan. 31, 2014; inventor: Reschke.
U.S. Appl. No. 14/173,391, filed Feb. 5, 2014; inventor: Kharin.
U.S. Appl. No. 14/176,341, filed Feb. 10, 2014; inventor: Hart.
U.S. Appl. No. 14/177,812, filed Feb. 11, 2014; inventor: Dycus.
U.S. Appl. No. 14/182,894, filed Feb. 18, 2014; inventor: Hart.
U.S. Appl. No. 14/182,967, filed Feb. 18, 2014; inventor: Latimer.
U.S. Appl. No. 14/183,090, filed Feb. 18, 2014; inventor: Arts.
U.S. Appl. No. 14/196,066, filed Mar. 4, 2014; inventor: McCullough.
U.S. Appl. No. 14/250,180, filed Apr. 10, 2014; inventor: Guerra.
U.S. Appl. No. 14/253,017, filed Apr. 15, 2014; inventor: Orszulak.
U.S. Appl. No. 14/260,905, filed Apr. 24, 2014; inventor: Jensen.
U.S. Appl. No. 14/268,051, filed May 2, 2014; inventor: Hart.
U.S. Appl. No. 14/268,140, filed May 2, 2014; inventor: Twomey.
U.S. Appl. No. 14/273,350, filed May 8, 2014; inventor: Gilbert.
U.S. Appl. No. 14/274,445, filed May 9, 2014; inventor: Hixson.
U.S. Appl. No. 14/276,465, filed May 13, 2014; inventor: Kappus.
U.S. Appl. No. 14/282,738, filed May 20, 2014; inventor: Rachlin.
U.S. Appl. No. 14/284,618, filed May 22, 2014; inventor: Hempstead.
U.S. Appl. No. 14/286,105, filed May 23, 2014; inventor: Johnson.
U.S. Appl. No. 14/294,316, filed Jun. 3, 2014; inventor: Johnson.
U.S. Appl. No. 14/295,049, filed Jun. 3, 2014; inventor: Couture.
U.S. Appl. No. 14/295,730, filed Jun. 4, 2014; inventor: Sartor.
U.S. Appl. No. 14/295,757, filed Jun. 4, 2014; inventor: McKenna.
U.S. Appl. No. 14/297,316, filed Jun. 5, 2014; inventor: Ackley.
U.S. Appl. No. 14/297,404, filed Jun. 5, 2014; inventor: Allen.
U.S. Appl. No. 14/299,740, filed Jun. 9, 2014; inventor: Larson.
U.S. Appl. No. 14/319,869, filed Jun. 30, 2014; inventor: Cunningham.
U.S. Appl. No. 14/322,513, filed Jul. 2, 2014; inventor: Duffin.
U.S. Appl. No. 14/335,303, filed Jul. 18, 2014; inventor: Lee.
Heniford et al. "Initial Research and Clinical Results with an Electrothermal Bipolar Vessel Sealer" Oct. 1999. (1 page).

SURGICAL INSTRUMENTS

CROSS REFERENCE TO RELATED APPLICATION

The present application claims the benefit of and priority to U.S. Provisional Application Ser. No. 62/055,011, filed on Sep. 25, 2014, the entire contents of which are incorporated herein by reference.

BACKGROUND

Technical Field

The present disclosure relates to surgical instruments. In particular, the present disclosure relates to a surgical instrument including a reusable handle and shaft assembly and a disposable end effector configured to be releasably coupled thereto.

Description of Related Art

Endoscopic forceps are commonly used in endoscopic surgical procedures to coagulate, cauterize and seal tissue. Such forceps typically include a pair of jaw members that can be controlled by a surgeon to grasp targeted tissue, such as, e.g., a blood vessel. Utilizing a movable handle of the forceps, the jaw members may be approximated toward one another to apply a mechanical clamping force to the tissue. The jaw members are typically associated with one or more electrodes to permit the delivery of electrosurgical energy to the tissue. The combination of mechanical clamping force and electrosurgical energy has been demonstrated to fuse adjacent layers of tissue captured between the jaw members with limited demarcation therebetween.

While this type of endoscopic forceps is suitable for its intended use, since it is typically disposable it is relatively expensive because it is not reusable after a surgical procedure.

SUMMARY

Accordingly, in view of at least the above drawbacks of wholly disposable endoscopic forceps, it would be desirable to construct endoscopic forceps having a reusable handle and shaft assembly and a disposable end effector assembly that can be easily releasably coupled to the reusable handle and shaft assembly.

Embodiments of the present disclosure are described in detail with reference to the drawing figures wherein like reference numerals identify similar or identical elements. As used herein, the term "distal" refers to a portion of a surgical instrument, including an end effector, handle assembly and/or elongated shaft thereof, that is being described which is further from a user, while the term "proximal" refers to a portion of a surgical instrument, including an end effector, handle assembly and/or elongated shaft thereof, that is being described which is closer to a user.

An aspect of the present disclosure provides an electrosurgical instrument, such as, for example, an endoscopic electrosurgical forceps. The forceps include a handle assembly or housing, an elongated shaft, a knife drive shaft, a jaw drive shaft, an end effector and a coupling member. The elongated shaft has a proximal end coupled to the housing and a distal end. The knife drive shaft is disposed within the housing and axially movable within the elongated shaft. The jaw drive shaft is disposed within the housing and axially movable within the elongated shaft. The end effector includes a pair of opposing jaw members, a knife member, and a driven member. The knife member has a proximal end and a distal end and is translatable through the jaw members. The proximal end is selectively engageable to a distal end of the knife drive shaft such that movement of the knife drive shaft moves the knife member. The driven member has proximal end distal ends. The proximal end is configured to operably couple to the jaw drive shaft and the distal end is configured to operably couple to the pair of jaw members such that movement of the driven member moves the pair of jaw members between an open configuration and a closed configuration. The coupling member is configured to releasably secure the end effector and the elongated shaft.

In some embodiments, the knife member may define an opening therein and the knife drive shaft may be rotatably engageable with the opening such that the end effector is rotatable about the knife drive shaft between an angled configuration with the elongated shaft and an aligned configuration with the elongated shaft. The knife member may rotatably engages an intermediate portion of the elongated shaft and the opening may be defined in a proximal end of the knife member. The opening may have an oblong configuration.

In some embodiments, the end effector may further include an outer cannulated shaft rotatably coupled to the pair of jaw members and may house a distal end of the knife member and the distal end of the driven member. A proximal end of the outer cannulated shaft may have a first pair of tabs extending laterally therefrom. The distal end of the elongated shaft may have a second pair of tabs extending laterally therefrom. Upon coupling the elongated shaft and the end effector, the first and second pairs of tabs may abut one another. The coupling member may include a pair of arms configured to overlap the first and second pairs of tabs such that the coupling member secures the elongated shaft and the end effector assembly upon engagement thereof. It is contemplated that the knife member may include an elongated slot defined therein. The coupling member may be configured for snap fit engagement with the outer cannulated shaft and the distal end of the elongated shaft.

In some embodiments, the end effector may include a pair of electrical leads coupled to the pair of jaw members. The elongated shaft may have a pair of electrical leads extending from the distal end thereof configured for releasable electrical connection to the pair of electrical leads of the end effector.

In another aspect of the present disclosure, an embodiment of a disposable end effector is disclosed. The end effector includes a pair of opposing jaw members, a knife member, a driven member, and an outer cannulated shaft. The knife member has a proximal end and a distal end. The knife member is translatable through at least one jaw member. The proximal end of the knife member is selectively engageable to a distal end of a knife drive shaft. The knife member includes an opening defined in the proximal end thereof. The driven member has a distal end configured to operably couple to the pair of jaw members such that movement of the driven member moves the pair of jaw members between an open configuration and a closed configuration. The outer cannulated shaft is rotatably coupled to the pair of jaw members that houses the distal end of the knife member and the distal end of the driven member.

In yet another aspect of the present disclosure, a method of assembling an electrosurgical instrument is provided. The method includes providing a housing having an elongated shaft extending therefrom; coupling a knife member of an end effector assembly to a knife drive shaft operably coupled to the housing of the electrosurgical instrument; rotating the end effector assembly relative to the knife drive shaft into coaxial alignment with the elongated shaft of the electrosurgical instrument; engaging a driven member of the end effector assembly with a jaw drive shaft operably coupled to the housing and axially movable within the elongated shaft; and attaching a coupling member to the end effector assembly and the elongated shaft to couple the end effector assembly with the elongated shaft.

In some embodiments, rotating the end effector assembly may engage the driven member with the jaw drive shaft.

BRIEF DESCRIPTION OF THE DRAWING

Various embodiments of the present disclosure are described hereinbelow with references to the drawings, wherein.

DETAILED DESCRIPTION

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

As described above, a surgical instrument including a reusable housing or handle assembly, an elongated shaft coupled to the handle assembly, and a disposable end effector assembly releasably coupleable to the elongated shaft may prove useful in the surgical arena, and such a surgical instrument is described herein.

Figure 1:
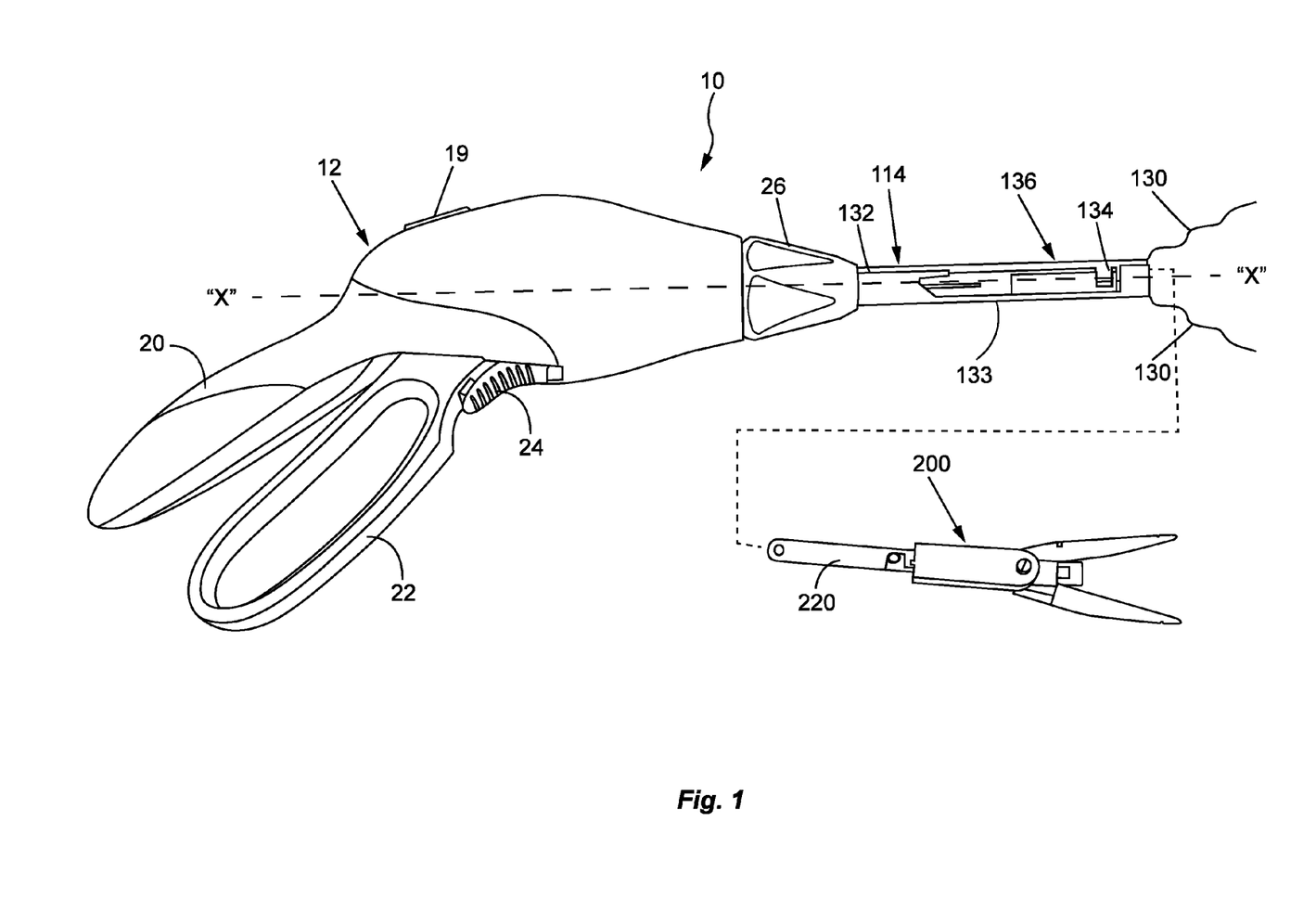
FIG. 1 is an elevation view, with parts separated, of an electrosurgical instrument with a selectively attachable end effector assembly according to an embodiment of the present disclosure.

Referring initially to FIG. 1, an electrosurgical instrument, such as, for example, electrosurgical forceps 10 generally includes a reusable housing or handle assembly 12 having a reusable elongated shaft 114 extending distally therefrom and a disposable end effector assembly 200 releasably coupled to a distal end 134 thereof. Handle assembly 12 supports various actuators thereon for remotely controlling end effector assembly 200 through elongated shaft 114. Although this configuration is typically associated with instruments for use in laparoscopic or endoscopic surgical procedures, various aspects of the present disclosure may be practiced with traditional open instruments and in connection with endoluminal procedures as well.

To mechanically control end effector assembly 200, handle assembly 12 supports a stationary handle 20, a movable handle 22, a trigger 24 and a rotation knob 26. The movable handle 22 is operable to move the end effector assembly 200 between an open configuration (FIG. 5A) wherein a pair of opposed jaw members 202a, 202b are disposed in spaced relation relative to one another, and a closed configuration (FIG. 5B) wherein jaw members 202a, 202b are approximated. Compression of the movable handle 22 relative to the stationary handle 20 moves the end effector assembly 200 to the closed configuration and release of the movable handle 22 from the stationary handle 20 moves the end effector assembly 200 to the open configuration. The trigger 24 is selectively operable to extend and retract a knife member 220 (see FIG. 3) through the end effector assembly 200 when the end effector assembly 200 is in the closed configuration. Actuation of the rotation knob 26 rotates elongated shaft 114 and end effector assembly 200 about a longitudinal axis "X" extending through forceps 10 (See FIG. 1).

To electrically control energy applied to each respective jaw member 202a, 202b of the end effector assembly 200, handle assembly 12 supports a depressible switch 19 thereon, which is operable by the user to initiate and terminate the delivery of electrosurgical energy (e.g., RF energy) to the end effector assembly 200. The switch 19 is in electrical communication with an electrosurgical generator (not shown) via suitable electrical wiring (not shown) extending from handle assembly 12. In some embodiments, end effector assembly 200 may be battery-powered. The switch 19 may be any suitable switch capable of electrically coupling the generator to the end effector assembly 200.

Figure 2:
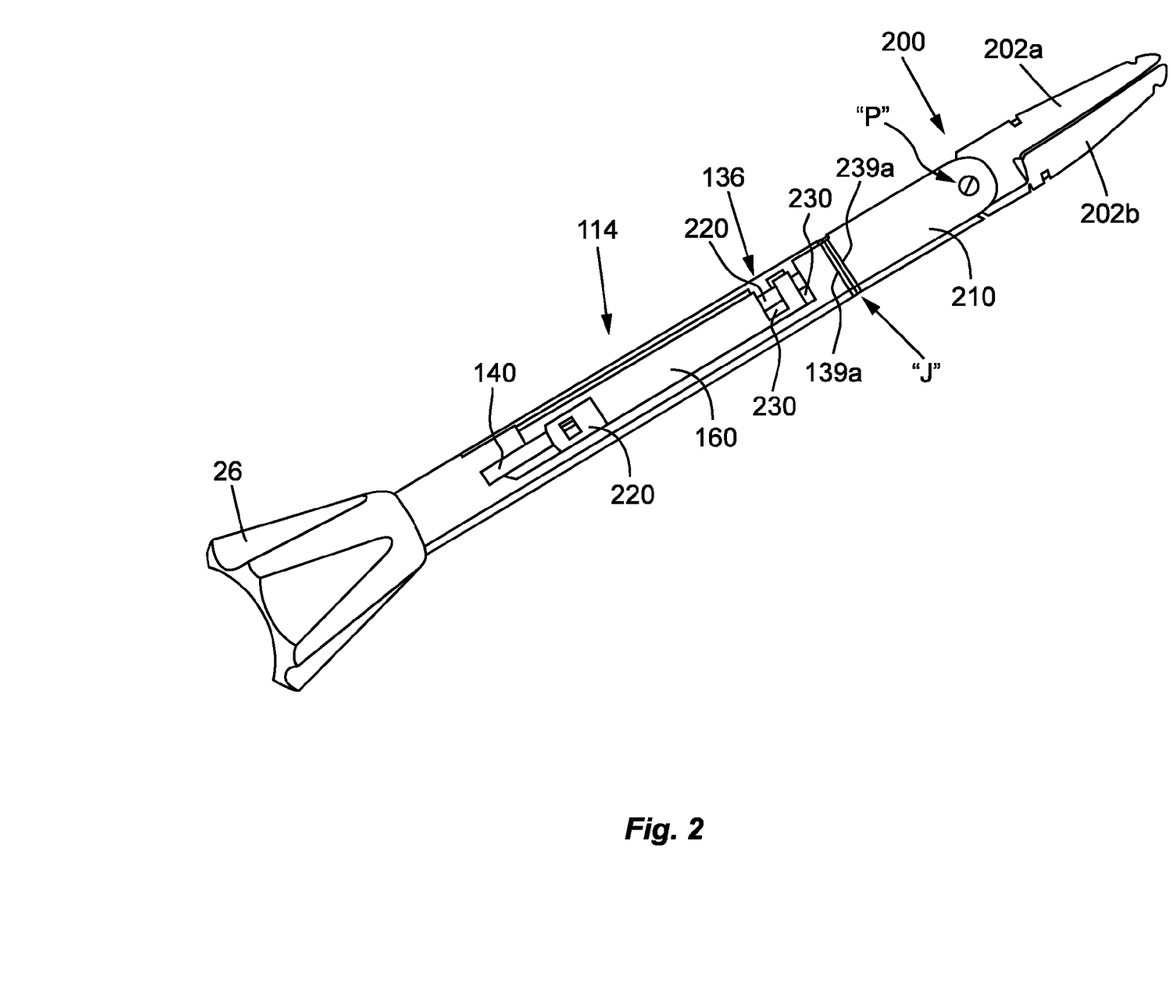
FIG. 2 is an enlarged, elevation view of the end effector assembly coupled to an elongated shaft of the electrosurgical instrument shown in FIG. 1.

Referring to FIGS. 1 and 2, elongated shaft 114 has a proximal end 132 and a distal end 134 and defines the longitudinal axis "X" therebetween. Elongated shaft 114 defines an elongated cavity 136 therein configured to house the internal components thereof, such as, for example, a knife drive shaft 140 and a jaw drive shaft 160. Elongated shaft 114 may include a cover 138 (FIG. 9) rotatably engaged thereto that covers cavity 136 during use of electrosurgical instrument 10. Proximal end 132 of elongated shaft 114 is coupled to handle assembly 12 and distal end 134 of elongated shaft 114 is configured to releasably couple to a proximal end 210a of the end effector assembly 200 shown in FIG. 6 via a coupling member 260, as described in greater detail below.

Figure 8:
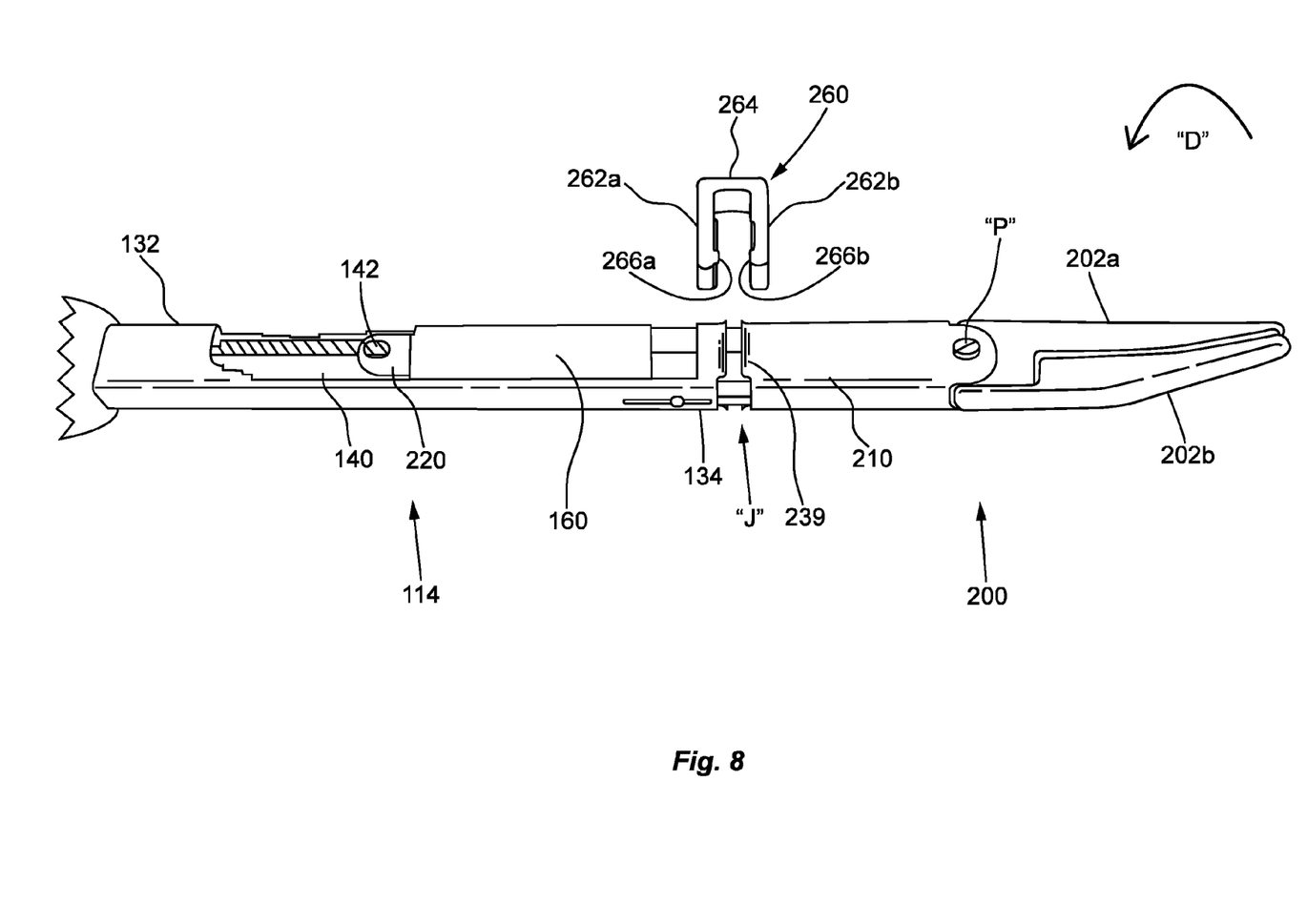
FIG. 8 is a plan view of a coupling member and the end effector assembly shown in position to lock the elongated shaft to the end effector assembly.

Proximal ends 204a, 204b of each jaw member 202a, 202b include an electrical lead 212 extending proximally therefrom and configured to mate with a corresponding electrical element of the elongated shaft 114. In particular, the electrical connection is made at a junction "J" (FIG. 5A) at which tabs 139a, 239a come together. One electrical lead 212 may be routed and electrically connected to a conductive pad on each tab 239a. There may be a mating conductive pad on each tab 139a of elongated shaft 114 so that when the two shaft sections 114, 210 are assembled, the electrical connection is made and held in place with coupling member 260 (FIG. 8).

Figure 3:
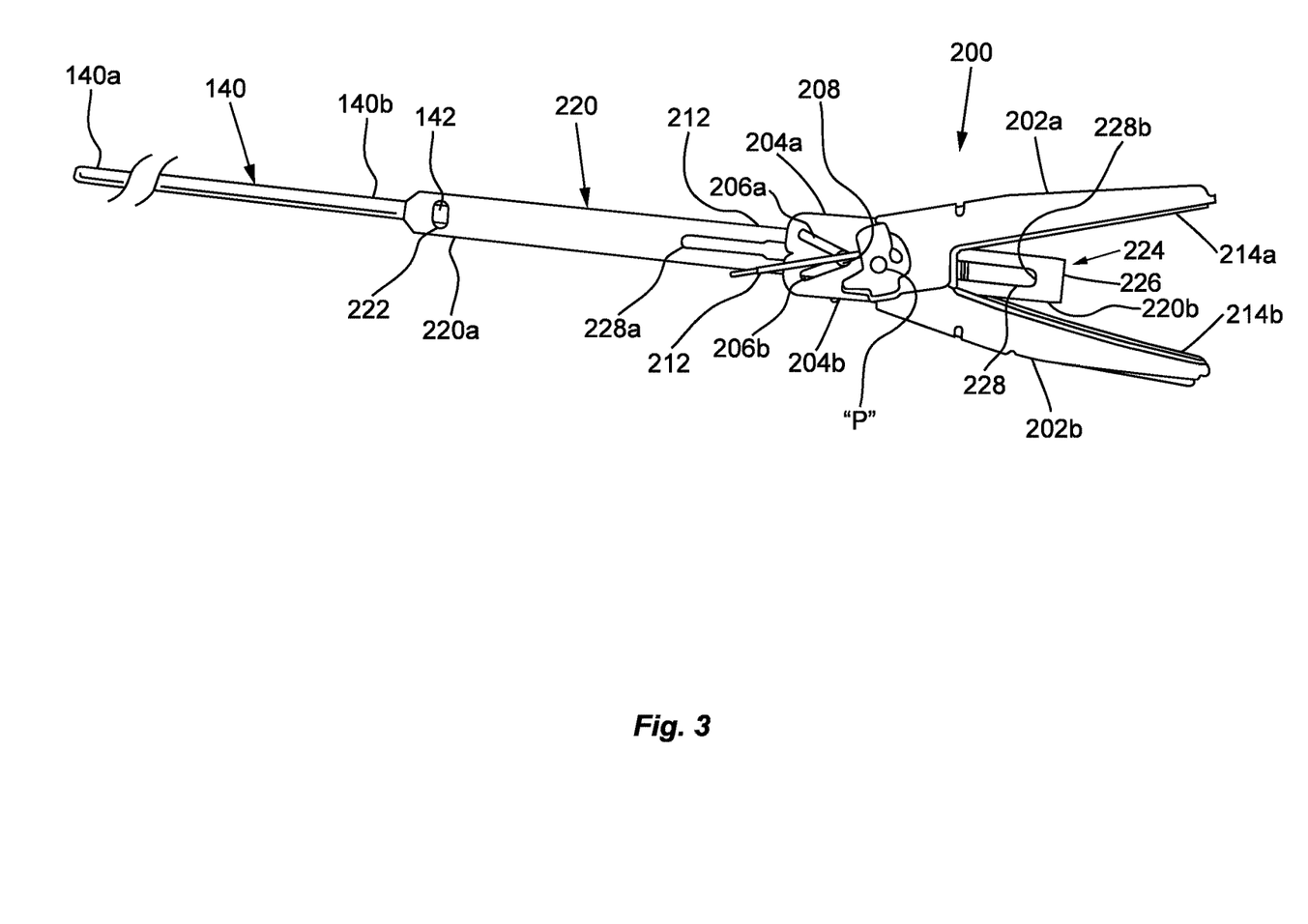
FIG. 3 is an enlarged, perspective view of the end effector assembly shown in FIG. 1 coupled to a knife drive shaft of the elongated shaft.

With reference to FIGS. 2-4, 5A, and 5B, elongated shaft 114 includes knife drive shaft 140 and jaw drive shaft 160 each being axially movable within elongated shaft 114 and along longitudinal axis "X." With specific reference to FIG. 3, knife drive shaft 140 has a proximal end 140a and a distal end 140b. Proximal end 140a of knife drive shaft 140 is operably coupled to handle assembly 12 such that an actuation of trigger 24 axially moves knife drive shaft 140 distally through elongated shaft 114. Distal end 140b of knife drive shaft 140 is configured for pivotable engagement with a knife member 220 of end effector assembly 200. Specifically, distal end 140b of knife drive shaft 140 includes a surface feature, such as, for example, a rounded projection 142. Projection 142 is disposed within an intermediate portion 133 of elongated shaft 114, spaced a predefined distance from distal end 134 of elongated shaft 114. Projection 142 is configured for disposal in an opening 222 defined in a proximal end 220a of knife member 220, as described in greater detail below, such that knife drive shaft 140 can selectively engage and drive axial movement of knife member 220 upon actuation of trigger 24 (see FIG. 7).

Figure 4:
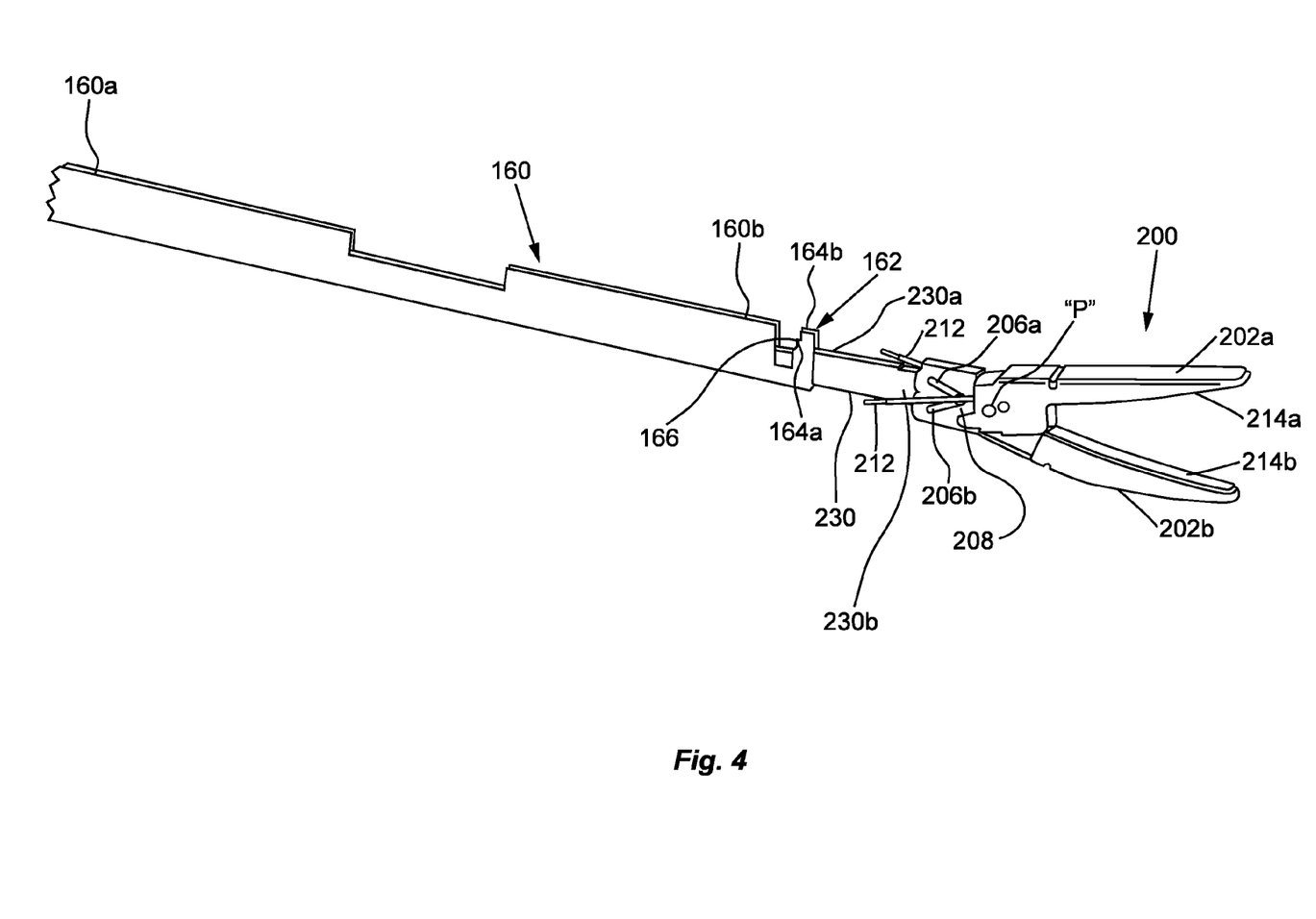
FIG. 4 is an enlarged, side view of the end effector assembly of FIG. 1 shown coupled to a jaw drive shaft of the elongated shaft.
Figure 7:
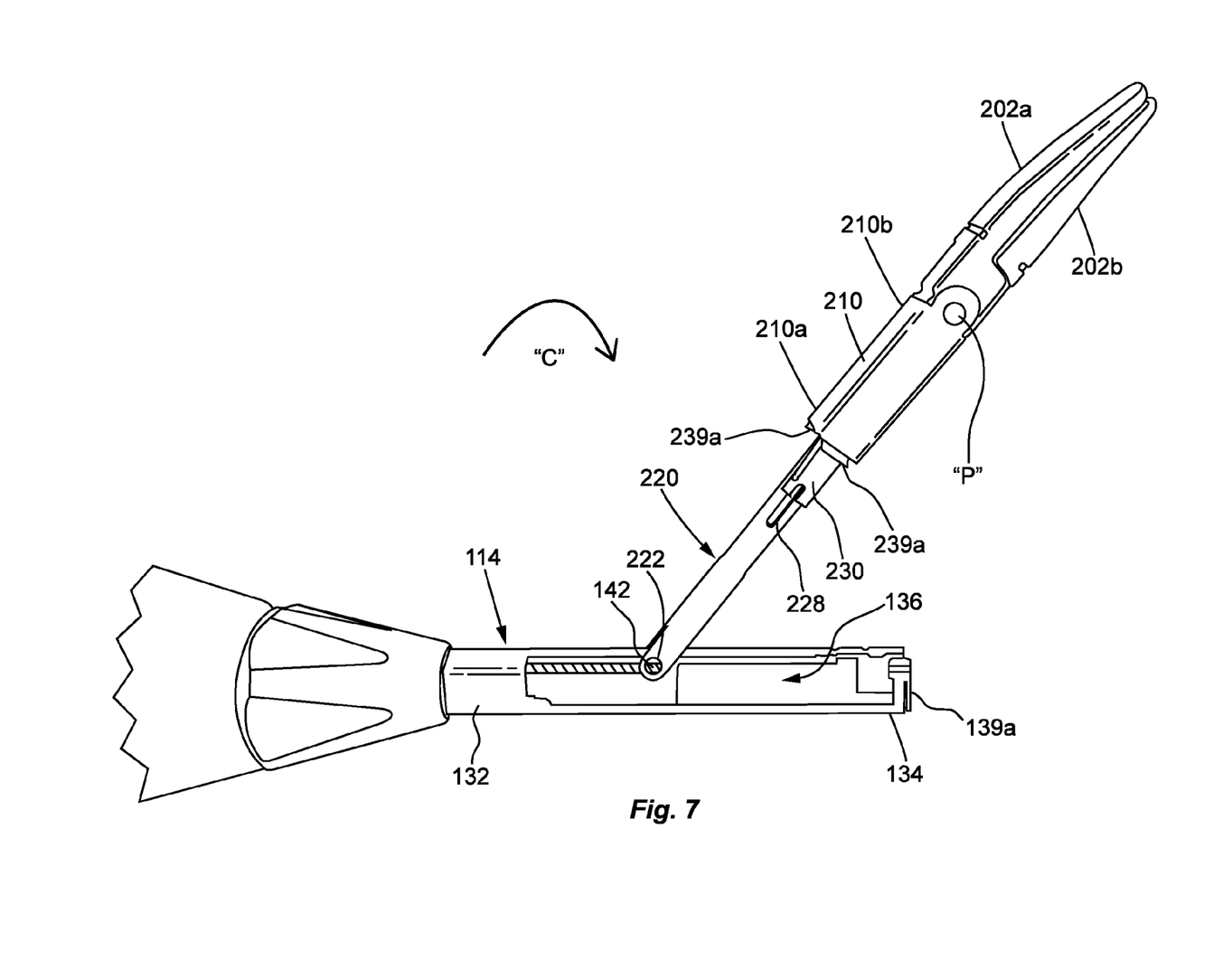
FIG. 7 is an enlarged, perspective view of the electrosurgical instrument shown in FIG. 1 illustrating a rotatable coupling of the end effector assembly with the elongated shaft.

With specific reference to FIG. 4, jaw drive shaft 160 includes a proximal end 160a and a distal end 160b. Proximal end 160a of jaw drive shaft 160 is operably coupled to handle assembly 12 such that an actuation of handle 22 relative to handle 20 axially moves jaw drive shaft 160 within elongated shaft 114 and along longitudinal axis "X." Distal end 160b of jaw drive shaft 160 includes a connection portion 162 configured to releasably engage a proximal end 230a of a driven member 230 of end effector assembly 200. Connection portion 162 includes a pair of resiliently biased fingers 164a, 164b defining a cavity 166 therebetween. Cavity 166 is adapted for disposal of proximal end 230a of driven member 230 of end effector assembly 200. In some embodiments, fingers 164a, 164b releasably capture proximal end 230a of driven member 230 to form a snap fit engagement between jaw drive shaft 160 and driven member 230. In other embodiments, jaw drive shaft 160 and driven member 230 can be configured for various engagements, such as, for example, frictional, pull and lock, compression fit, or the like. In one embodiment, the proximal end 230a of driven member 230 includes a t-shaped flange that is configured to be rotatingly received within cavity 166 as best shown in FIGS. 7 and 8.

Figure 5A:
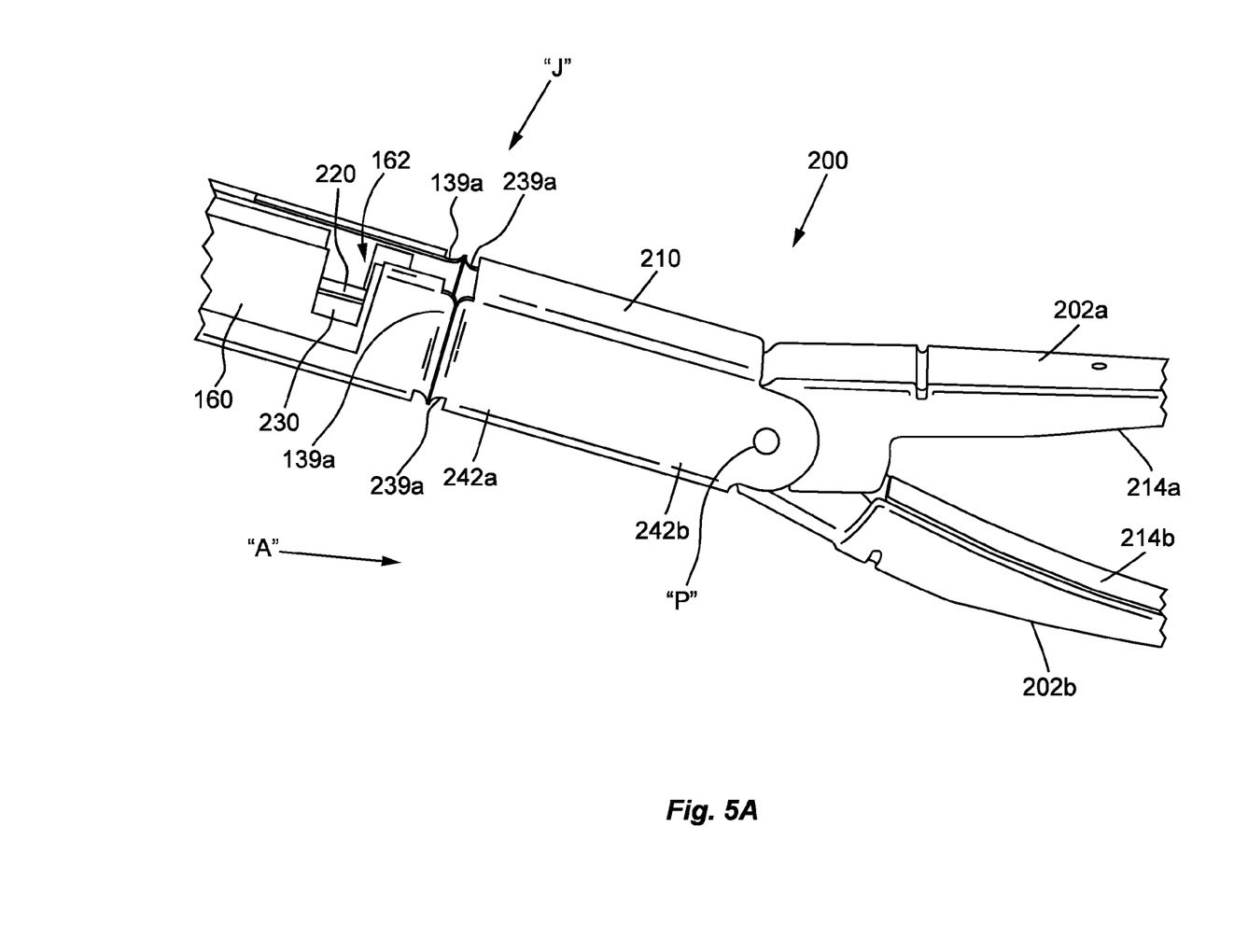
FIGS. 5A and 5B are enlarged, perspective views of the elongated shaft and end effector assembly shown in FIG. 1 illustrating opening and closing of end effector assembly via movement of the jaw drive shaft shown in FIG. 4.
Figure 5B:
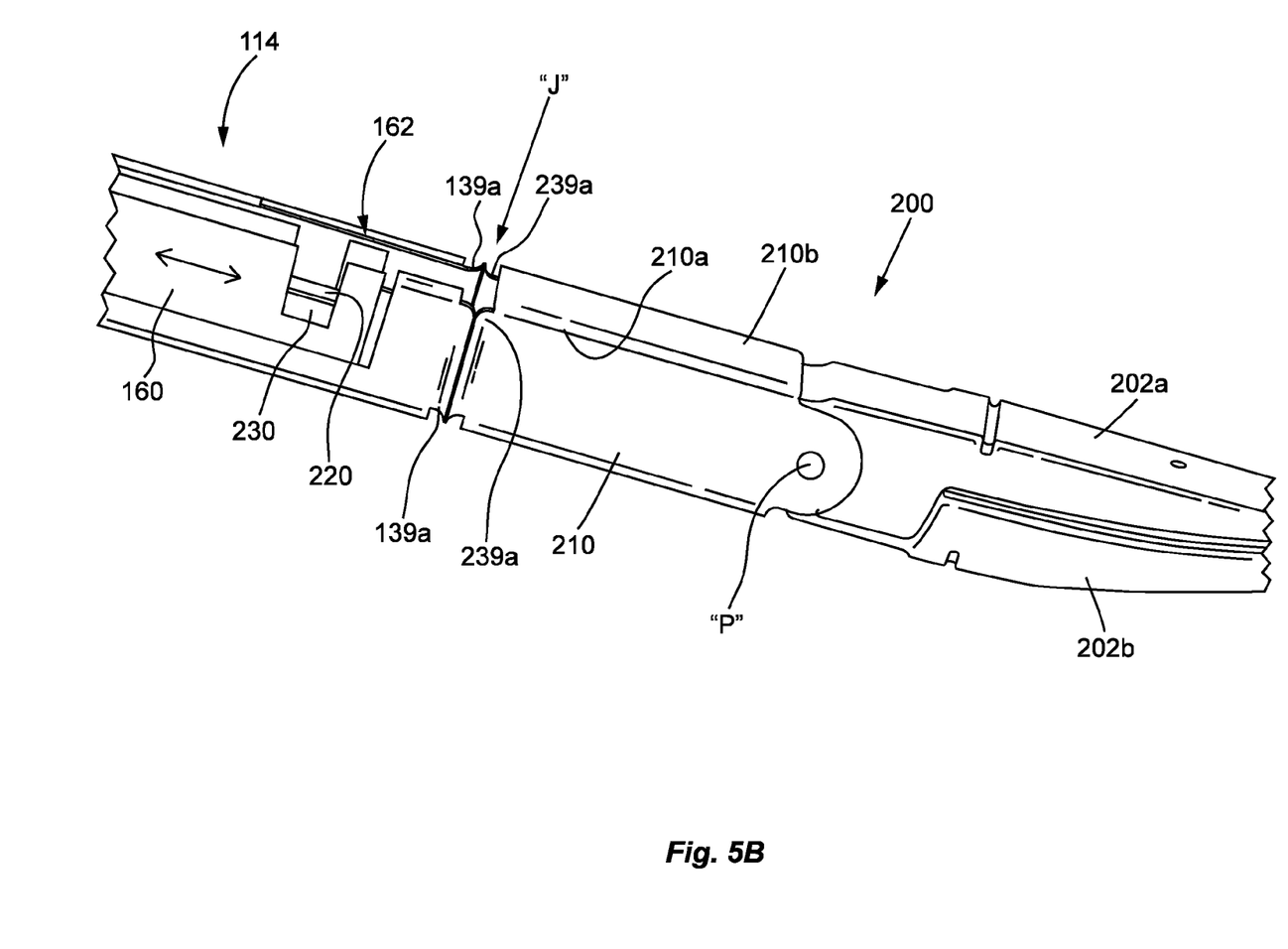

In use, upon an actuation of handle assembly 12, jaw drive shaft 160 moves along longitudinal axis "X," in a direction indicated by arrow "A" in FIG. 5A, via the operable coupling of jaw drive shaft 160 with handle assembly 12. The axial movement or translation of jaw drive shaft 160 within elongated shaft 114 drives concomitant axial movement of driven member 230 to move jaw members 202a, 202b of end effector assembly 200 from an open configuration, as shown in FIG. 5A, to a closed configuration, as shown in FIG. 5B, to clamp tissue disposed between jaw members 202a, 202b.

With reference to FIGS. 3-6, electrosurgical forceps 10 further includes an outer cannulated shaft 210 attached to jaw members 202a, 202b. Proximal ends 204a, 204b of jaw members 202a, 202b each define a cam slot 206a, 206b adapted for sliding disposal of a pivot bar 208 of driven member 230 to open and close jaw members 202a, 202b upon translation of driven member 230 therethrough. Upon distal translation of driven member 230, jaw members 202a, 202b pivot about a pivot point "P" relative to one another to clamp tissue disposed therebetween.

The upper and lower jaw members 202a, 202b include electrical leads 212a and 212b extending proximally therefrom. Tissue-engaging sealing plates 214a, 214b are disposed on the lower and upper jaw members 202a, 202b, respectively, and are electrically coupled to opposite terminals, e.g., positive or active (+) and negative or return (−) terminals associated with the generator. Thus, bipolar energy may be provided to the sealing plates 214a, 214b and through tissue. Alternatively, sealing plates 214a, 214b may be configured to deliver monopolar energy to tissue. In a monopolar configuration, one or both sealing plates 214a, 214b deliver electrosurgical energy from an active terminal, e.g., (+), while a return pad (not shown) is placed generally on a patient and provides a return path to the opposite terminal, e.g., (−), of the generator.

With specific reference to FIG. 3, end effector assembly 200 includes knife member 220, which extends between jaw members 202a, 202b and is axially movable or translatable between jaw members 202a, 202b. Knife member 220 has an elongated configuration and has a proximal end 220a and a distal end 220b. Proximal end 220a of knife member 220 defines an oblong opening 222 therein configured for rotatable receipt of projection 142 of knife drive shaft 140 as explained above. Opening 222 may be suitably configured, such as, for example, oval, rectangular, tapered, variable, uniform, non-uniform, and/or elongated. Upon insertion of projection 142 of knife drive shaft 140 within opening 222 of knife member 220, knife member 220 can be rotated relative to knife drive shaft 140 between a non-locking, angled configuration with elongated shaft 114, as shown in FIG. 7, and a locking, aligned configuration with elongated shaft 114, as shown in FIG. 8, as described in greater detail below.

Distal end 220b of knife member 220 has a distal-most edge 224 that defines a sharp surface or blade 226 thereon configured to axially slice through tissue. Knife member 220 further defines an elongated slot 228 therein. It is contemplated that pivot bar 208, which drives the opening and closing of jaw members 202a, 202b about pivot point "P," extends through the elongated slot 228 such that knife member 220 can translate over pivot bar 208 between proximal and distal limits 228a, 228b of elongated slot 228. In this way, upon actuation of trigger 24, knife member 220 axially translates through elongated shaft 114 to displace blade 226 from a proximal position between jaw members 202a, 202b toward a distal position between jaw members 202a, 202b and to slice through tissue disposed between jaw members 202a, 202b.

With specific reference to FIG. 4, end effector assembly 200 includes driven member 230, which is configured to open and close jaw members 202a, 202b upon axial movement of jaw drive shaft 160. Driven member 230 has a proximal end 230a and a distal end 230b. Proximal end 230a of driven member 230 is configured to releasably engage connection portion 162 of jaw drive shaft 160 such that driven member 230 is movable by jaw drive shaft 160. Distal end 230b of driven member 230 is operably coupled to jaw members 202a, 202b such that axial movement of driven member 230, via axial translation of jaw drive shaft 160, moves or translates pivot bar 208 through cam slots 206a, 206b of jaw members 202a, 202b to open and close jaw members 202a, 202b.

Figure 6:
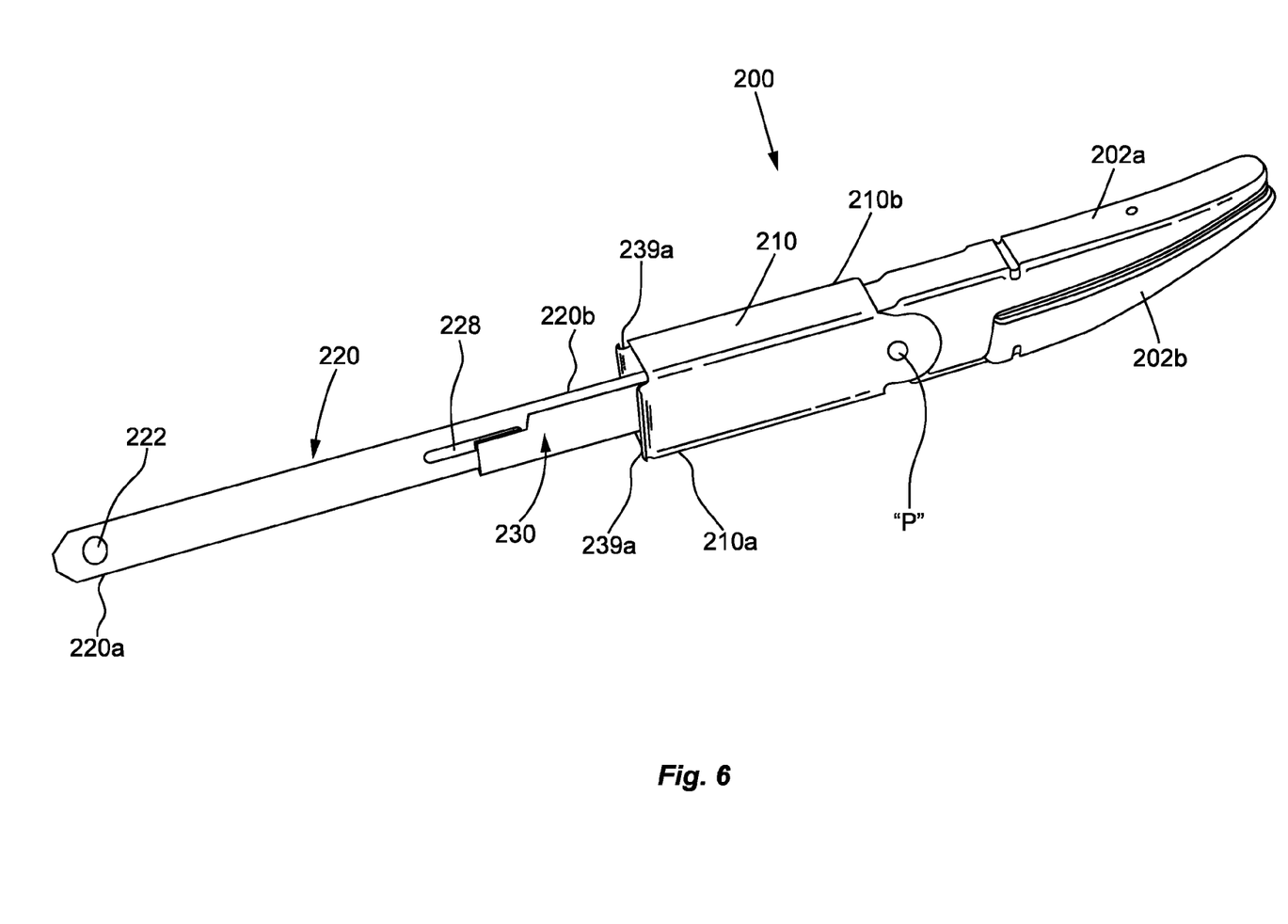
FIG. 6 is an enlarged, perspective view of the end effector assembly shown in FIG. 1.

With continued reference to FIGS. 5A, 5B, and 6, end effector assembly 200 further includes outer cannulated shaft 210, which houses distal end 220b of knife member 220 and distal end 230b of driven member 230. Cannulated shaft 210 has a proximal end 242a and a distal end 242b. As briefly mentioned above, proximal end 242a includes a pair of tabs 239a extending laterally therefrom. Tabs 239a abut against tabs 139a of elongated shaft 114 upon coupling of end effector assembly 200 with elongated shaft 114, as shown in FIGS. 5A and 5B. Distal end 242b of cannulated shaft 210 includes two pivot points "P" having jaw members 202a, 202b rotatably coupled therewith. Jaw members 202a, 202b pivot relative to one another about pivot points "P" of cannulated shaft 210.

In use, projection 142 of knife drive shaft 140 is inserted within opening 222 defined in proximal end 220a of knife member 220 and end effector assembly 200 is rotated, in a direction indicated by arrow "C" in FIG. 7, through cavity 136 defined in elongated shaft 114 and toward a locking configuration with elongated shaft 114, in which end effector assembly 200 and elongated shaft 114 are in coaxial alignment, as shown in FIG. 8. Upon entering the locking configuration, tabs 239a of end effector assembly 200 abut tabs 139a of elongated shaft 114 and proximal ends 220a, 230a of knife member 220 and driven member 230, respectively, are disposed within elongated shaft 114. The rotation of end effector assembly 200, in the direction indicated by arrow "C," also couples proximal end 230a of driven member 230 with connection portion 162 of jaw drive shaft 160 to releasably fix driven member 230 with jaw drive shaft 160. To secure or lock end effector assembly 200 with elongated shaft 114, a coupling member 260 is connected at the junction "J" of elongated shaft 114 and end effector assembly 200, as described in greater detail below. Upon locking engagement of end effector assembly 200 with elongated shaft 114, surgical instrument 10 is assembled for use.

Figure 9:
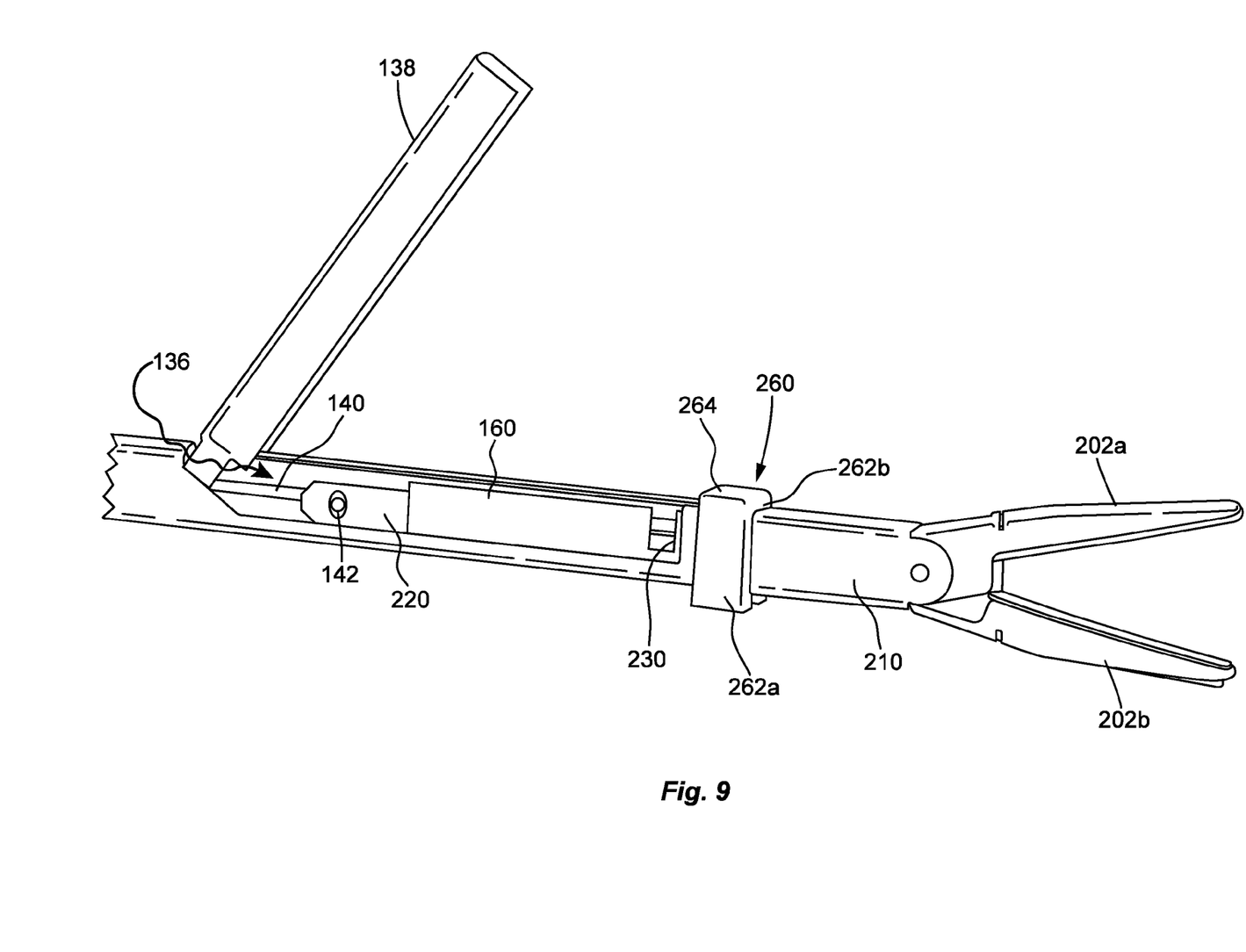
FIG. 9 is an enlarged, perspective view of the coupling member releasably locking the elongated shaft with the end effector assembly and a cover disposed in an open position.

With reference to FIGS. 8 and 9, coupling member 260 releasably connects distal end 134 of elongated shaft 114 and proximal end 242a of end effector assembly 200. Specifically, coupling member 260 includes a pair of spaced apart, parallel arms 262a, 262b extending from a top portion or hood 264 thereof. Arms 262a, 262b are spaced from one another a distance substantially equal to a width of distal end 134 of elongated shaft 114. Coupling member 260 may be fabricated from a material that allows arms 262a, 262b to flex relative to one another to fit securely (e.g., a snap fit engagement) around the junction "J" of elongated shaft 114 and end effector assembly 200. Arms 262a, 262b each have a flange 266a, 266b extending around perimeters thereof and toward and interior of coupling member 260. Flanges 266a, 266b are configured to extend underneath bottom portions of both elongated shaft 114 and end effector assembly 200 upon connection of coupling member 260 with junction "J." Flanges 266a, 266b are also configured to overlap tabs 139a of elongated shaft 114 and tabs 239a of end effector assembly 200 to retain tabs 139a, 239a within coupling member 260 such that relative axial movement of elongated shaft 114 and end effector assembly 200 is resisted and/or prevented by coupling member 260.

In some embodiments, portions or an entirety of coupling member 260 can have various material properties, such as, for example, rigid, flexible, adhesive and/or memory shape. It is further contemplated that coupling member 260 generally has a squared configuration corresponding to a squared configuration of elongated shaft 114 and/or end effector assembly 200. In some embodiments, coupling member 260 may be suitably configured so as to correspond to various configurations of elongated shaft 114 and/or end effector assembly 200.

In operation, arms 262a, 262b of coupling member 260 overlap tabs 139a, 239a of elongated shaft 114 and end effector assembly 200 to capture tabs 139a, 239a therein and releasably lock end effector assembly 200 to elongated shaft 114. Upon connecting coupling member 260 with elongated shaft 114 and end effector assembly 200 at junction "J," surgical instrument 10 is assembled for use. Prior to use of surgical instrument 10, cover 138 of elongated shaft 114 is moved to a closed position to cover cavity 136, thereby enclosing internal components of elongated shaft 114 to prevent exposure of the internal components to surgical debris.

In some embodiments, after use of surgical instrument 10, end effector assembly 200 may be disposed of and handle assembly 12 and elongated shaft 114 may be reused after sterilization. To remove end effector assembly 200 from elongated shaft 114, arms 262a, 262b of coupling member 260 are flexed outwardly to detach coupling member 260 from elongated shaft 114 and end effector assembly 200. End effector 200 is rotated, in a direction indicated by arrow "D" in FIG. 8, which detaches driven member 230 from connection portion 162 of jaw drive shaft 160. Projection 142 of knife drive shaft 140 is released from opening 222 of knife member 220, thereby detaching end effector assembly 200 from elongated shaft 114. End effector assembly 200 is then discarded.

The various embodiments disclosed herein may also be configured to work with robotic surgical systems and what is commonly referred to as "Telesurgery." Such systems employ various robotic elements to assist the surgeon in the operating theatre and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

In particular, the transmission assemblies of the present disclosure may be configured for use with such robotic systems in addition to being used with manually-operated assemblies. That is, depending on the particular procedure, the transmission assembly may be coupled to a manually-operated assembly or a robotic system. Thus, the transmission assemblies of the present disclosure are capable of being used in either configuration without the need for multiple transmission assemblies depending on whether robotic or manual surgery is desired.

With respect to coupling the transmission assembly to a robotic system, the robotic system would include suitable components, such as those detailed above, capable of manipulating and actuating the transmission assembly. The robotic surgical systems may further be employed with one or more consoles that are next to the operating theater or located in a remote location. In this instance, one team of surgeons or nurses may prep the patient for surgery and configure the robotic surgical system with one or more of the transmission assemblies while another surgeon (or group of surgeons) remotely control the transmission assembly(s) via the robotic surgical system. As can be appreciated, a highly skilled surgeon may perform multiple operations in multiple locations without leaving his/her remote console which can be both economically advantageous and a benefit to the patient or a series of patients.

In use, the robotic arms of the surgical system are typically coupled to a pair of master handles by a controller. The handles can be moved by the surgeon to produce a corresponding movement, manipulation, and/or actuation of the transmission assembly(s) coupled thereto. The movement of the master handles may be scaled so that the operably components of the transmission assembly(s) has a corresponding movement that is different, smaller or larger, than the movement performed by the operating hands of the surgeon. The scale factor or gearing ratio may be user-adjustable so that the operator can control the resolution of the operable components of the transmission assembly(s).

The master handles of the robotic system may further include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

From the foregoing and with reference to the various figure drawings, those skilled in the art will appreciate that certain modifications can also be made to the present disclosure without departing from the scope of the same.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical instrument, comprising:
   a housing;
   an elongated shaft having a proximal end coupled to the housing and a distal end;
   a knife drive shaft disposed within the housing and axially movable within the elongated shaft;
   a jaw drive shaft disposed within the housing and axially movable within the elongated shaft;
   an end effector assembly including:
      a pair of opposing jaw members;
      a knife member having a proximal end and a distal end, the knife member translatable through at least one jaw member, the proximal end of the knife member selectively engageable to a distal end of the knife drive shaft such that movement of the knife drive shaft moves the knife member, wherein the knife member defines an opening therein and the knife drive shaft is configured to rotatably engage the opening such that the end effector assembly is rotatable about the knife drive shaft between an angled configuration with the elongated shaft and an aligned configuration with the elongated shaft; and
      a driven member having proximal and distal ends, the proximal end of the driven member configured to operably couple to the jaw drive shaft and the distal end of the driven member configured to operably couple to the pair of jaw members such that movement of the driven member moves the pair of jaw members between an open configuration and a closed configuration; and
   a coupling member configured to releasably secure the end effector assembly and the elongated shaft.

2. The electrosurgical instrument according to claim 1, wherein the knife member rotatably engages an intermediate portion of the elongated shaft and the opening is defined in a proximal end of the knife member.

3. The electrosurgical instrument according to claim 2, wherein the opening has an oblong configuration.

4. The electrosurgical instrument according to claim 1, wherein the end effector assembly further includes an outer cannulated shaft rotatably coupled to the pair of jaw members that houses a distal end of the knife member and the distal end of the driven member.

5. The electrosurgical instrument according to claim 4, wherein a proximal end of the outer cannulated shaft has a first pair of tabs extending laterally therefrom and the distal end of the elongated shaft has a second pair of tabs extending laterally therefrom, wherein upon coupling the elongated shaft and the end effector assembly, the first and second pairs of tabs abut one another.

6. The electrosurgical instrument according to claim 5, wherein the coupling member includes a pair of arms configured to overlap the first and second pairs of tabs such that the coupling member secures the elongated shaft and the end effector assembly upon engagement thereof.

7. The electrosurgical instrument according to claim 4, wherein the knife member includes an elongated slot defined therein.

8. The electrosurgical instrument according to claim 4, wherein the coupling member is configured for snap fit engagement with the outer cannulated shaft and the distal end of the elongated shaft.

9. The electrosurgical instrument according to claim 1, wherein the end effector assembly includes a pair of electrical leads coupled to the pair of jaw members and the elongated shaft has a pair of electrical leads extending from the distal end thereof configured for releasable electrical connection to the pair of electrical leads of the end effector assembly.

10. The electrosurgical instrument according to claim 1, wherein each of the knife member and the driven member defines a longitudinal axis, the longitudinal axis of the knife member being parallel with the longitudinal axis of the driven member.

11. The electrosurgical instrument according to claim 1, wherein the proximal end of the driven member extends proximally beyond a proximal end of the pair of opposing jaw members.

12. A disposable end effector assembly, comprising:
    a pair of opposing jaw members;
    a knife member having a proximal end and a distal end, the knife member translatable through at least one jaw member, the proximal end of the knife member selectively engageable to a distal end of a knife drive shaft, the knife member including an opening defined in the proximal end thereof, the opening configured for rotatable engagement with the knife drive shaft such that the end effector assembly is rotatable about the knife drive shaft between an angled configuration with the knife drive shaft and an aligned configuration with the knife drive shaft;
    a driven member having a distal end configured to operably couple to the pair of jaw members such that movement of the driven member moves the pair of jaw members between an open configuration and a closed configuration; and
    an outer cannulated shaft rotatably coupled to the pair of jaw members that houses the distal end of the knife member and the distal end of the driven member.

13. The end effector assembly according to claim 12, wherein the opening has an oblong configuration.

14. The end effector assembly according to claim 12, wherein the knife member includes an elongated slot defined therein.

15. The end effector assembly according to claim 12, wherein a proximal end of the outer cannulated shaft includes a pair of tabs extending laterally therefrom.

16. The end effector assembly according to claim 12, further including a pair of electrical leads coupled to the jaw members.

17. The end effector assembly according to claim 12, wherein each of the knife member and the driven member defines a longitudinal axis, the longitudinal axis of the knife member being parallel with the longitudinal axis of the driven member.

18. The end effector assembly according to claim 12, wherein the driven member has a proximal end extending proximally beyond a proximal end of the pair of opposing jaw members.

* * * * *